United States Patent
Ruffa

(10) Patent No.: US 8,306,763 B1
(45) Date of Patent: Nov. 6, 2012

(54) PARTICLE CHARACTERIZATION VIA DOPPLER DISTRIBUTION

(75) Inventor: Anthony A. Ruffa, Hope Valley, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 314 days.

(21) Appl. No.: 12/700,987

(22) Filed: Feb. 5, 2010

(51) Int. Cl.
  *G01N 15/00* (2006.01)
  *G01N 11/00* (2006.01)
(52) U.S. Cl. ............... 702/54; 702/189; 73/865.5
(58) Field of Classification Search ........... 702/54, 702/189; 73/865.5
  See application file for complete search history.

(56) References Cited

U.S. PATENT DOCUMENTS

| | | | |
|---|---|---|---|
| 4,412,451 A | 11/1983 | Uusitalo et al. | |
| 4,739,662 A | 4/1988 | Foote | |
| 4,986,659 A * | 1/1991 | Bachalo | 356/336 |
| 5,121,629 A | 6/1992 | Alba | |
| 5,831,150 A | 11/1998 | Sowerby et al. | |
| 6,191,853 B1 | 2/2001 | Yamaguchi et al. | |
| 6,983,208 B2 | 1/2006 | Metcalf et al. | |
| 7,047,809 B2 | 5/2006 | Cobb | |
| 7,331,233 B2 | 2/2008 | Scott | |
| 2004/0006436 A1 * | 1/2004 | Morgen et al. | 702/48 |
| 2006/0178581 A1 | 8/2006 | Africk et al. | |

* cited by examiner

*Primary Examiner* — Michael Nghiem
*Assistant Examiner* — L. Anderson
(74) *Attorney, Agent, or Firm* — James M. Kasischke; Michael P. Stanley; Jean-Paul A. Nasser

(57) ABSTRACT

Systems and methods are provided for determining information about particle geometry are provided. As such, an ultrasonic transducer acts as both a transmitter and a receiver. The transducer insonifies a particle and scattered waves are then received by the transducer—now acting as a receiver. A small flat target moving relative to a stationary receiver will lead to the same radiated field as waves propagating through an equivalent moving aperture. Based on the Doppler distribution of the scattered or radiated waves resulting from relative motion between the particles and a receiver, the acoustic pressure field in the plane of the equivalent two-dimensional aperture can be inferred. The equivalent aperture geometry can be obtained from the inferred field. Hence, the particle geometry can be determined.

6 Claims, 3 Drawing Sheets

PARTICLE CHARACTERIZATION VIA DOPPLER DISTRIBUTION

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention relates to characterization of particles, and more specifically to a system and method for determining information about particle geometry based on the Doppler distribution of scattered or radiated waves resulting from relative motion between the particles and a receiver.

(2) Description of the Prior Art

A wide variety of industrial processes require non-contact measurement of materials, including separation processes, agglomeration reactors, milling operations and polymerization. For such applications, there is a need for the characterization of physical properties such as particle sizes.

Various apparatus and methods for composition and particle size measurement utilizing ultrasound are known in the art. In addition, various methods describe the use of attenuation at two discrete frequencies to monitor mean particle size in a slurry. Generally, the particle size distributions are determined by assuming a starting particle distribution; predicting attenuation at each discrete frequency; comparing the predicted attenuations with actual attenuation measurements; adjusting the distribution and then repeating this procedure until a suitable match is achieved between prediction and measurement.

Such methods have a disadvantage in that a large number of physical properties of the particles and suspending medium must be known to make the predictions. In addition, the numerical computations required to calculate the theoretical attenuations are time-consuming, and often unstable.

Those skilled in the art readily understand the wide range of potential applications for particle sizing measurements in various industries such as food, mining, pharmaceuticals, chemicals and petroleum. As such, what are needed are methods and systems for particle characterization that minimize or overcome the problems discussed above.

SUMMARY OF THE INVENTION

It is therefore a general purpose and primary object of the present invention to provide a system and method for inferring information about particle geometry based on the Doppler distribution of scattered or radiated waves resulting from relative motion between the particles and a receiver.

In order to attain the object described, an ultrasonic transducer is provided that acts as a transmitter and receiver. The transducer insonifies a particle, and scattered waves are then received by the transducer now acting as a receiver.

Using the measured Doppler distribution, the acoustic pressure field in the plane of the two-dimensional aperture can be inferred. Since it is known that a small flat target moving relative to a stationary receiver will lead to the same radiated field as waves propagating through an equivalent moving aperture; then accordingly, the aperture geometry (in this case the particle geometry) can be determined.

In one embodiment, a method for determining information about particle geometry includes insonifying a particle; measuring a Doppler distribution of waves scattered from the particle; comparing the Doppler distribution to a lookup table distributions; and obtaining the particle geometry from the distribution best matching the Doppler distribution.

In one embodiment, the method includes generating lookup table distributions. Generating the lookup table distributions includes obtaining the lookup table distributions, $p(x,y,z,t)$, from the relationship $$p(x, y, z, t) = \frac{e^{-i\omega_0 t}}{2\pi} \int_{-\infty}^{\infty}\int_{-\infty}^{\infty} P(k_x, k_y) e^{-ik_x x} e^{-ik_y y} e^{iz\sqrt{k^2-k_x^2-k_y^2}} dk_x dk_y,$$

where $P(k_x,k_y)$ is a spatial Fourier transform of an acoustic pressure field for a given aperture corresponding to a particular particle geometry, p is the acoustic pressure, k, and $k_y$ are the wave numbers in the x and y directions, t is time, z is the coordinate perpendicular to the aperture, x and y are coordinates in the plane of the aperture, and $\omega_0$ is the frequency.

In one embodiment, a method for inferring information about particle geometry includes insonifying a particle; measuring a Doppler distribution of acoustic pressure waves scattered from the particle given by $p(x,y,z,t)$; and determining the particle geometry based on the relationship $$p(x, y, z, t) = \frac{e^{-i\omega_0 t}}{2\pi} \int_{-\infty}^{\infty}\int_{-\infty}^{\infty} P(k_x, k_y) e^{-ik_x x} e^{-ik_y y} e^{iz\sqrt{k^2-k_x^2-k_y^2}} dk_x dk_y,$$

where $P(k_x,k_y)$ is a spatial Fourier transform of an acoustic pressure field for a given aperture corresponding to the particle geometry.

In some embodiments, measuring further includes adjusting an axis of insonification to maximize an extent of the Doppler distribution and determining the amount of adjustment.

In one embodiment, a system for inferring information about particle geometry includes a sonic wave transmitter that insonifies a particle; a receiver that measures a Doppler distribution of waves scattered from the particle; and a processor that compares the Doppler distribution to lookup table distributions.

In one embodiment, the system further includes a processor program product disposed on a processor readable medium, and having instructions for causing the processor to generate the lookup table distributions, $p(x,y,z,t)$, from the relationship $$p(x, y, z, t) = \frac{e^{-i\omega_0 t}}{2\pi} \int_{-\infty}^{\infty}\int_{-\infty}^{\infty} P(k_x, k_y) e^{-ik_x x} e^{-ik_y y} e^{iz\sqrt{k^2-k_x^2-k_y^2}} dk_x dk_y,$$

where $P(k_x,k_y)$ is a spatial Fourier transform of an acoustic pressure field for a given aperture corresponding to a particular particle geometry. In some embodiments, the transmitter and the receiver comprise an ultrasonic transducer.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DETAILED DESCRIPTION OF THE INVENTION

Figure 1:
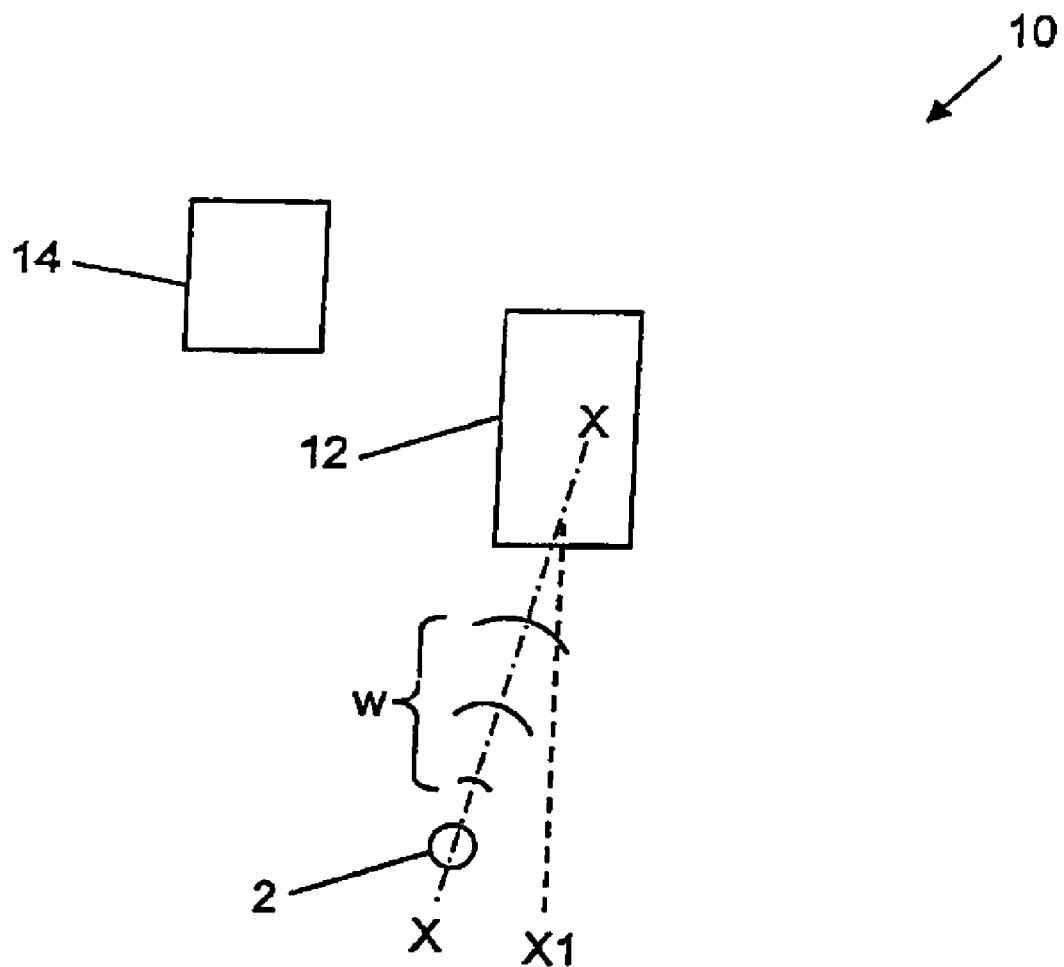
FIG. 1 depicts a system for obtaining particle geometry information.

As is known in the art, diffraction causes bending of sound waves. Diffraction can affect Doppler Shifts when there is relative motion between a source and a receiver. The change in Doppler shifts is due to the fact that the received signal is not in the form of a plane wave. Rather, the received signal has some characteristics of a spherical wave.

As is also known in the art, a spherical wave can be shown to be the summation of plane waves propagating in all directions (the Weyl integral). Plane waves propagating at an angle with respect to the receiver will have a lower group velocity than those waves that propagate normal to the receiver. Thus, there will be a continuous distribution of Doppler Shifts due to plane waves arriving at different angles with respect to the receiver. However, the distribution of Doppler Shifts will occur only under diffraction-dominated conditions (i.e., when the effective radius of the object is on the order of a wavelength and the distance between the object and receiver is small enough so that the wave-front curvature is still important). When diffraction effects are important, the Doppler distribution (which is governed by the particle geometry) can be used to infer information about the particle geometry.

According to Babinet's principle, a small flat target moving relative to a stationary receiver will lead to the same radiated field as waves propagating through an equivalent moving aperture. Therefore, the field radiated from a simplified particle can be analyzed using the result of a plane wave propagated through an equivalent aperture. Three-dimensional particles introduce further complications that generally require numerical modeling. However, much of the physics of a three-dimensional particle can be captured with a simplified two-dimensional model.

It has been shown that the acoustic field due to diffraction by an aperture in a two-dimensional infinite screen is:

$$p(x, y, z, t) = \frac{e^{-i\omega_0 t}}{2\pi} \int_{-\infty}^{\infty} \int_{-\infty}^{\infty} P(k_x, k_y) e^{-ik_x x} e^{-ik_y y} e^{iz\sqrt{k^2 - k_x^2 - k_y^2}} \, dk_x dk_y. \quad (1)$$

Here $P(k_x, k_y)$ is the spatial Fourier transform of the acoustic pressure field p in the plane of the two-dimensional aperture (z=0). This expression satisfies both the Helmholtz equation, $\nabla^2 p + k^2 p = 0$, and the boundary conditions, which consist of the acoustic pressure p specified at z=0 (both on the aperture and on the screen).

The diffracted field can be interpreted as an angular spectrum of plane waves—a continuous distribution of plane waves originating from the screen wherein the direction of propagation varies from being perpendicular to being parallel to the screen. The group velocity of the diffracted field thus assumes a continuous distribution.

In the far field, the integration limits can be truncated to ±k ($k=\omega_0/C$, where C is the speed of sound) since energy at higher wavenumbers is evanescent or nonpropagating in nature. Further assuming that $P(k_x,k_y)$ is an even function (for illustration purposes) leads to:

$$p(x, y, z, t) = \qquad (2)$$
$$\frac{2}{\pi} e^{-i\omega_0 t} \int_0^k \int_0^k P(k_x, k_y) \cos(k_x x) \cos(k_y y) e^{iz\sqrt{k^2 - k_x^2 - k_y^2}} \, dk_x dk_y.$$

The integrand represents a summation of pairs of plane waves oriented at varying (opposite) angles with respect to the planar screen, wherein each pair has the form:

$$\cos(k_x x)\cos(k_y y) e^{iz\sqrt{k^2 - k_x^2 - k_y^2}}. \qquad (3)$$

Each pair propagates at a phase velocity given by:

$$u_p = c\sqrt{1 - (k_x^2 + k_y^2)/k^2}, \qquad (4)$$

and a group velocity of $$u_g = c\sqrt{1 - (k_x^2 + k_y^2)/k^2}. \qquad (5)$$

The process of separating the acoustic field into pairs of plane waves can be visualized more clearly using the method of exhaustion, an expansion for Riemann integrals having the form:

$$\int_0^b f(x)dx = b \sum_{n=1}^{\infty} \sum_{m=1}^{2^n - 1} (-1)^{m+1} 2^{-n} f(mb/2^n). \qquad (6)$$

Applying this to Equation (2) leads to:

$$p(x, y, z, t) = \qquad (7)$$
$$\frac{2k^2}{\pi} e^{i\omega_0 t} \sum_{n=1}^{\infty} \sum_{m=1}^{2^n - 1} \sum_{q=1}^{\infty} \sum_{p=1}^{2^q - 1} (-1)^{m+p+1} 2^{-n-q} P(mk/2^n, pk/2^q) \times$$
$$\cos(mkx/2^n)\cos(pky/2^q) e^{izk\sqrt{1 - (mk/2^n)^2 - (pk/2^q)^2}}$$

Each pair of terms in this infinite series represents a pair of plane waves propagating at equal and opposite angles with respect to the screen that contains the equivalent aperture that represents the target by Babinet's principle. Depending on the pair of plane waves, the phase velocity varies from c to ∞, while the group velocity varies from 0 to c. The relationship between the phase and group velocity is similar to that of a waveguide having a constant cross-section. However a significant difference is that a waveguide has discrete modes (due to finite dimensions) while an aperture has a continuous distribution of modes.

The group velocity distribution leads to a distribution in Doppler shifts when there is relative motion between the aperture and the receiver. An aperture moving relative to a stationary receiver with a velocity $u_r$, leads to a received frequency of $f_o(1+u_r/u_g)$ for the pair of plane waves having a group velocity of $u_g$. For a circular aperture, the acoustic pressure can be expressed in polar coordinates as follows (Doppler effects included):

$$p(r, z, t) = \frac{2}{\pi} \int_0^{2\pi} \int_0^{k(1+u_r/c)} P(\kappa) e^{-i\kappa x \cos\theta} e^{-i\kappa y \sin\theta} \quad (8)$$

$$e^{iz\sqrt{k^2-\kappa^2}} \times e^{-i\omega_0 t \left(1+u_r c^{-1}/\sqrt{1-\kappa^2/k^2}\right)} \kappa d\kappa d\theta, \text{ or}$$

$$p(r, z, t) = \quad (9)$$

$$4 \int_0^{k(1+u_r/c)} P(\kappa) J_0(\kappa r) e^{iz\sqrt{k^2-\kappa^2}} e^{-i\omega_0 t \left(1+u_r c^{-1}/\sqrt{1-\kappa^2/k^2}\right)} \kappa d\kappa,$$

where $r = \sqrt{x^2+y^2}$ and $$k = \sqrt{k_x^2 + k_y^2}.$$

The temporal Fourier transform of Equation (9) is as follows, Equation (10)

$$\prod(r, z, \omega) = 8\pi \int_0^{k(1+u_r/c)} P(\kappa) J_0(\kappa r) \quad (10)$$

$$e^{iz\sqrt{k^2-\kappa^2}} \times \delta(\omega - \omega_0 (1 + u_r c^{-1}/\sqrt{1-\kappa^2/k^2})) \kappa d\kappa$$

After some algebraic manipulation:

$$\prod(r, z, \omega) = \quad (11)$$

$$8\pi \int_0^{k(1+u_r/c)} P\left(k\sqrt{1 - \frac{u_r^2 k^2}{(\alpha-\omega_0)^2}}\right) J_0\left(kr\sqrt{1 - \frac{u_r^2 k^2}{(\alpha-\omega_0)^2}}\right) \times$$

$$e^{izu_r k^2/(\alpha-\omega_0)} \delta(\omega - \alpha) \frac{u_r^2 k^4}{(\alpha-\omega_0)^3} d\alpha, \text{ or}$$

$$\prod(r, z, \omega) = 8\pi P\left(k\sqrt{1 - \frac{u_r^2 k^2}{(\omega-\omega_0)^2}}\right) \quad (12)$$

$$J_0\left(kr\sqrt{1 - \frac{u_r^2 k^2}{(\omega-\omega_0)^2}}\right) \times e^{izu_r k^2/(\omega-\omega_0)} \frac{u_r^2 k^4}{(\omega-\omega_0)^3};$$

where $\omega \geq \omega_0(1+u_r/c)$. When both the aperture and $u_r$ are small (and p is uniform on the aperture and zero outside the aperture at z=0), $\Pi$ can be approximated as follows:

$$\prod(r, z, \omega) \cong 8\pi P(0) J_0(kr) e^{izu_r k^2/(\omega-\omega_0)} \frac{u_r^2 k^4}{(\omega-\omega_0)^3}, \text{ or} \quad (13)$$

$$\left|\prod(r, z, \omega)\right| \cong 8\pi P(0) J_0(kr) \frac{u_r^2 k^4}{(\omega-\omega_0)^3}. \quad (14)$$

The minimum Doppler shift is $\Delta\omega = \omega_0 u_r/c$, identical to that when there is no distribution. At this Doppler shift, the spatial Fourier transform in Equation (12) reduces to P(0). When $\Delta\omega = \omega_0 u_r/c$ the amplitude of the Doppler distribution is estimated by Equation (14) to be ⅛ that of the minimum Doppler shift (or 9 dB lower), and the power (proportional to the square of the pressure amplitude) is 18 dB lower.

With a sufficient signal-to-noise ratio, the Doppler distribution should be measurable, allowing the possibility of inferring $P(k_x, k_y)$, and thus the aperture geometry from a single receiver. However, if the radius is large relative to a wavelength, then P in Equation (12) approaches zero quickly as ω increases from $\omega_0$, so that the distribution will be so narrow in frequency extent that the distribution probably cannot be measured. In this case, the only added information is that the effective particle radius is large compared to a wavelength.

The above analysis of an aperture moving relative to a stationary receiver can also be used for an equivalent particle that is moving relative to a stationary receiver—again by Babinet's principle.

Referring now to FIG. 1, there is depicted a system 10 for obtaining particle geometry information. In the system, an ultrasonic transducer 12 acts as both a transmitter and a receiver. Acting as a transmitter, the transducer 12 insonifies a particle 2. Acting as a receiver, the transducer 12 receives waves, w, scattered by the particle 2 and measures the Doppler distribution of the energy scattered from the particle.

As described in the above analysis, inferring $P(k_x, k_y)$ based on the measured Doppler distribution spectrum can lead to information on the particle geometry, in addition to relative velocity of the particle. This can be done with lookup tables of solutions providing Doppler distributions for circular apertures of various radii—as well as and also for other shapes. Such lookup tables can be generated from the above analysis given the aperture or particle geometry.

A processor 14 is in communication with the transducer 12 and receives data from the transducer 12. The processor 14 compares the measured Doppler distribution to known distributions in the lookup tables. The particle geometry corresponding to the distribution in the lookup table that best matches the measured distribution is taken as the geometry for the particle 2.

Figure 2:
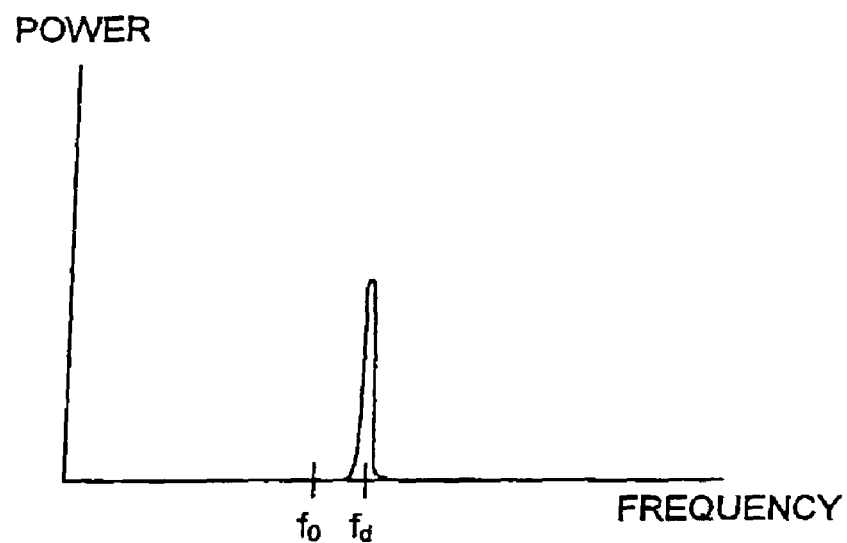
FIG. 2 is an exemplary plot of a Doppler shift for a large particle.
Figure 3:
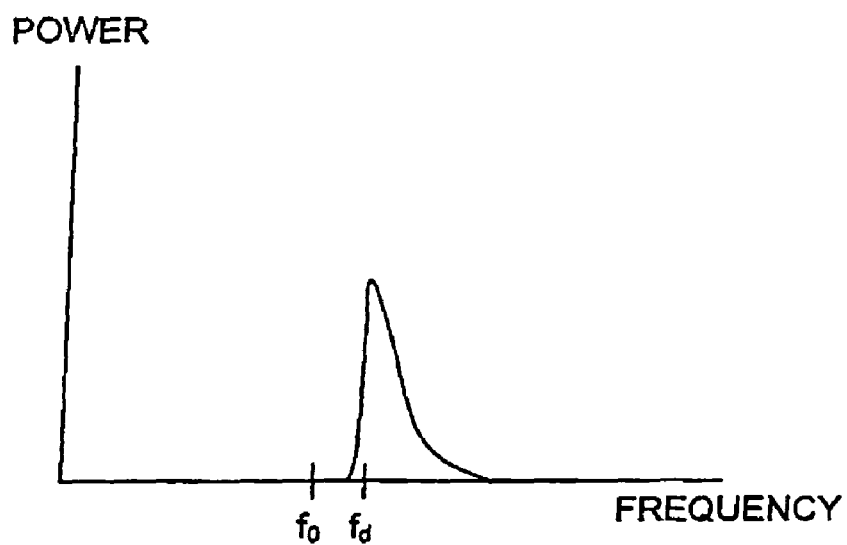
FIG. 3 is an exemplary plot of Doppler distribution for a particle having an effective radius on the order of a wavelength in size.

FIG. 2 and FIG. 3 show examples of Doppler distributions. FIG. 2 illustrates a single and discrete Doppler shift for a narrowband pulse for a particle having a size too large to exhibit an effect. FIG. 3 illustrates a Doppler distribution wherein the effective particle radius is on the order of a wavelength in size.

In many cases, an irregularly-shaped particle can be approximated as an equivalent flat circular particle. Lookup tables can also be included incorporating irregular shapes. When three-dimensional effects are important, lookup tables can be generated with finite element models for spheres and other important shapes.

In addition to obtaining particle geometry information, the system 10 can be used to localize particles, such as the particle 2, to a greater degree of accuracy than otherwise possible. This localization can be accomplished by taking advantage of diffraction effects as seen from the second term (Bessel function $J_0$) in Equation (12). When the particle moves from r=0, the value of the Bessel function term changes quickly.

Referring back to FIG. 1, the particle 2 can be localized by adjusting the transducer 12 until the particle lies along axis, X, so that the extent of the Doppler distribution is maximized. In FIG. 1, the adjustment is illustrated by dotted line x1. In this case, the transducer 12 acts as a continuous array steered in the broadside direction. The distance from x1 to axis X can be directly inferred using Equation (12). With an array of receivers, a particle moving across the received beams can be localized in "r" more precisely by the variation in the Doppler distribution.

The maximum distance, L, between the particle 2 and the transducer is governed by $L \leq d^2/8\lambda$, wherein d is the receiver diameter of the transducer and $\lambda$ is the acoustic wavelength. At this distance, the wavefront curvature will lead to a phase difference of 2n between the center of the transducer (12) and an edge of the transducer. For example, a 2 MegaHertz (MHz) transducer having a diameter of one inch will lead to a maximum distance of 4 inches. To increase the maximum distance, a higher frequency transducer can be used.

Figure 4:
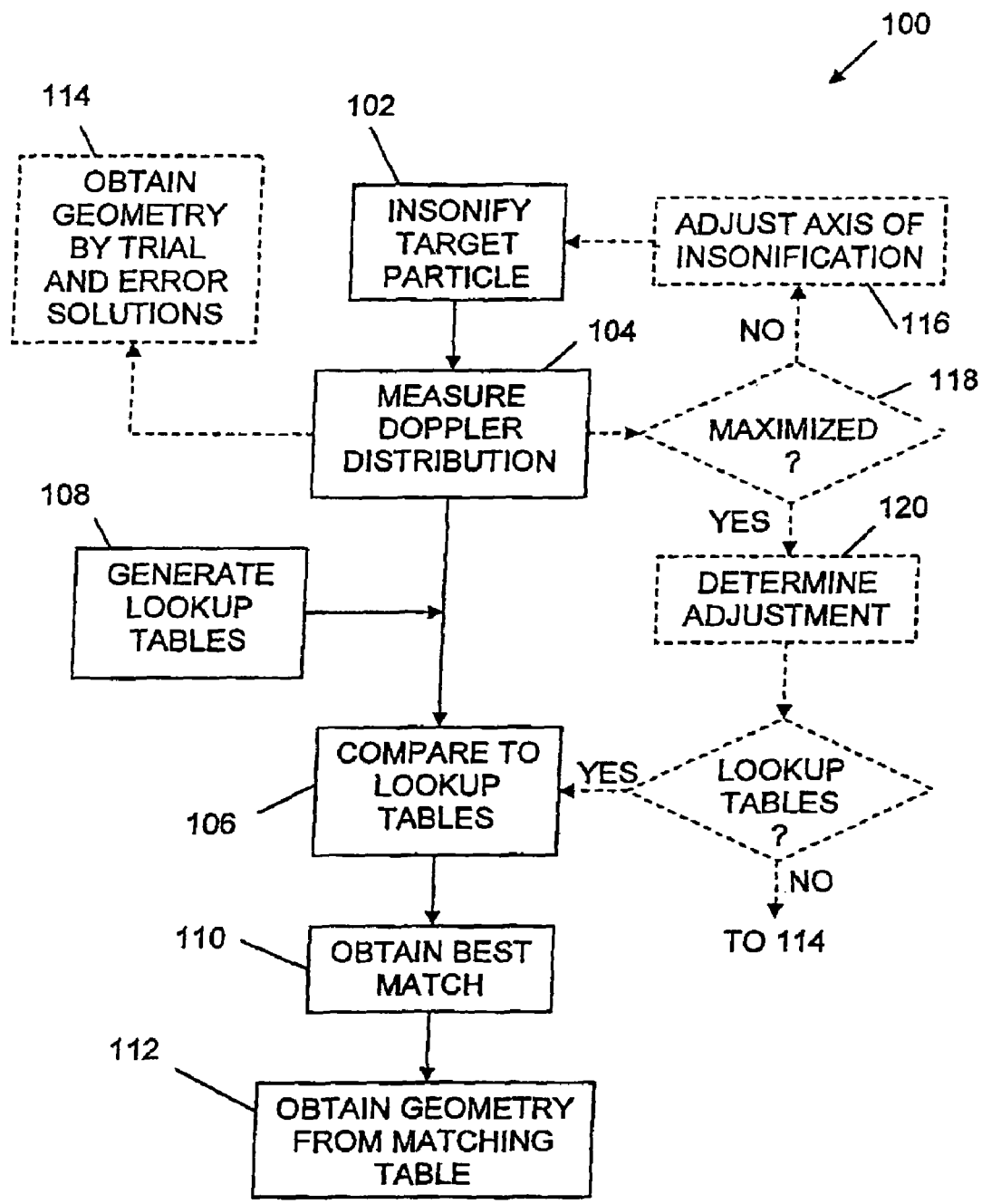
FIG. 4 depicts a block diagram of a method for obtaining particle geometry information.

Referring now to FIG. 4, there is shown a block diagram of method 100 for obtaining information about particle geometry. At block 102, a particle is insonified. The Doppler distribution of the scattered or radiated waves from the particle resulting from relative motion between the particle and the transducer is measured at block 104.

The measured Doppler distribution is compared to distribution lookup tables at block 106. The lookup tables are generated (block 108) from the above analysis given the aperture or particle geometry. For example, p(x,y,z,t) can be determined from Equation (1) knowing $P(k_x,k_y)$. The lookup tables can be generated at any point prior to the comparison step of block 106. The distribution in the lookup tables best matching the measured distribution is obtained at block 110. The particle geometry corresponding to the best matching lookup table distribution is obtained from the lookup table at block 112.

What have thus been described are systems and methods for inferring information about particle geometry. A transducer insonifies a particle and then measures the Doppler distribution of the scattered or radiated waves resulting from relative motion between the particle 2 and the transducer 12. The measured Doppler distribution is compared to distribution lookup tables. The particle geometry for the distribution in the lookup table best matching the measured distribution is taken as the geometry of the insonified particle.

Obviously many modifications and variations of the present invention may become apparent in light of the above teachings. For example, the system 10 can include a separate transmitter and a separate receiver instead of the transducer 12 being both a transmitter and receiver. Furthermore, the processor 14 can be incorporated into the transducer 12, or vice versa.

Additionally, the method 100 can infer the particle geometry directly from the measured distribution without the use of lookup tables. As shown in phantom form in FIG. 4; once the Doppler distribution is measured at block 104, trial and error solutions for P(0) and the corresponding particle geometry can be obtained (block 114) from Equation (14). However, it is recognizable to those skilled in the art that such solutions can be computationally intense.

Still further, the method 100 can localize the particle (shown in phantom in FIG. 4) by adjusting the axis of the insonification of the particle (block 116) until the extent of the Doppler distribution is maximized at block 118. At block 120, the amount of adjustment is directly inferred using Equation (12). Upon determining the adjustment, the particle geometry can be obtained as described previously (blocks 106, 114).

In light of the above, it is therefore understood that within the scope of the appended claims, the invention may be practiced otherwise than as specifically described.

What is claimed is:

1. A method for determining information about particle geometry, said method comprising the steps of:
   insonifying only a single particle;
   measuring a Doppler distribution of waves scattered from the particle;
   generating a lookup table of known distributions;
   comparing the Doppler distribution to the lookup table distributions; and
   obtaining the particle geometry from the lookup table distributions to match the Doppler distribution;
   wherein said generating step comprises the step of obtaining the lookup table distributions, p(x,y,z,t), from the relationship $$p(x, y, z, t) = \frac{e^{-i\omega_0 t}}{2\pi} \int_{-\infty}^{\infty} \int_{-\infty}^{\infty} P(k_x, k_y) e^{-ik_x x} e^{-ik_y y} e^{iz\sqrt{k^2 - k_x^2 - k_y^2}} dk_x dk_y,$$

where $P(k_x, k_y)$ is a spatial Fourier transform of an acoustic pressure field for a given aperture corresponding to a particular particle geometry.

2. A method according to claim 1, wherein said measuring step further comprises the steps of:
   adjusting an axis of insonification to maximize an extent of the Doppler distribution; and
   determining a location of the axis from said adjusting steps.

3. A method for determining information about particle geometry, said method comprising the steps of:
   insonifying only a single particle;
   measuring a Doppler distribution of waves scattered from the particle, p(x,y,z,t); and
   determining the particle geometry based on the relationship $$p(x, y, z, t) = \frac{e^{-i\omega_0 t}}{2\pi} \int_{-\infty}^{\infty} \int_{-\infty}^{\infty} P(k_x, k_y) e^{-ik_x x} e^{-ik_y y} e^{iz\sqrt{k^2 - k_x^2 - k_y^2}} dk_x dk_y,$$

where $P(k_x, k_y)$ is a spatial Fourier transform of an acoustic pressure field for a given aperture corresponding to the particle geometry.

4. A method according to claim 3, wherein said measuring step further comprises the steps of:
   adjusting an axis of insonification to maximize an extent of the Doppler distribution; and
   determining an amount of adjustment.

5. A system for inferring information about particle geometry, said system comprising:
   a sonic wave transmitter;
   a receiver;
   a processor; and
   a processor program product disposed on a processor readable medium, and having instructions for causing the processor to generate lookup table distributions, p(x,y,z,t), from the relationship $$p(x, y, z, t) = \frac{e^{-i\omega_0 t}}{2\pi} \int_{-\infty}^{\infty} \int_{-\infty}^{\infty} P(k_x, k_y) e^{-ik_x x} e^{-ik_y y} e^{iz\sqrt{k^2 - k_x^2 - k_y^2}} dk_x dk_y,$$

where $P(k_x, k_y)$ is a spatial Fourier transform of an acoustic pressure field for a given aperture corresponding to a particular particle geometry wherein said transmitter insonifies only a single particle, the receiver measures a Doppler distribution of waves scattered from the particle, and the processor compares the Doppler distribution to the lookup table distribution.

6. A system according to claim 5, wherein said transmitter and said receiver comprise an ultrasonic transducer.

* * * * *